United States Patent [19]

Andrews

[11] Patent Number: 5,225,163
[45] Date of Patent: Jul. 6, 1993

[54] REACTION APPARATUS EMPLOYING GRAVITATIONAL FLOW

[75] Inventor: Robert R. Andrews, Norfolk, Mass.

[73] Assignee: Angenics, Inc., Cambridge, Mass.

[21] Appl. No.: 873,710

[22] Filed: Apr. 22, 1992

Related U.S. Application Data

[63] Continuation of Ser. No. 395,751, Aug. 18, 1989, abandoned.

[51] Int. Cl.$^5$ .................. G01N 21/00; G01N 31/22
[52] U.S. Cl. ......................... 422/61; 422/58; 422/99; 422/100; 422/102
[58] Field of Search ............ 422/55, 58, 61, 99, 422/100, 102; 435/810; 436/808

[56] References Cited

U.S. PATENT DOCUMENTS

| | | | |
|---|---|---|---|
| 3,036,894 | 5/1962 | Forestiere | 422/61 X |
| 3,649,462 | 3/1972 | Jessup | 435/809 X |
| 3,799,742 | 3/1974 | Coleman | 422/61 |
| 3,888,629 | 6/1975 | Bagshawe | . |
| 4,088,448 | 5/1978 | Lilja et al. | . |
| 4,330,627 | 5/1982 | Thomas et al. | 422/61 X |
| 4,775,515 | 10/1988 | Cottingham | . |
| 4,806,316 | 2/1989 | Johnson et al. | 422/61 X |
| 4,868,129 | 9/1989 | Gibbons et al. | 436/179 |
| 5,019,351 | 5/1991 | Schulz | 422/58 X |

FOREIGN PATENT DOCUMENTS

| | | |
|---|---|---|
| 0153110 | 8/1985 | European Pat. Off. ........ 422/58 |
| 0212314 | 7/1986 | European Pat. Off. . |
| 0305210 | 3/1987 | European Pat. Off. . |
| 0339277 | 3/1989 | European Pat. Off. . |
| 90/09596 | 8/1990 | PCT Int'l Appl. . |

*Primary Examiner*—James C. Housel
*Assistant Examiner*—Arlen Soderquist
*Attorney, Agent, or Firm*—Hamilton, Brook, Smith & Reynolds

[57] ABSTRACT

A diagnostic device provides the flow of a desired reaction mixture under the force of gravity through a channel. The flow of the reaction mixture gains necessary energy to bring about a physical or a chemical reaction of the reaction mixture. A viewing chamber at the end of the channel retains results of the reaction. The device allows a timed reaction to take place without application of external forces such as vibration, rocking, optical activation, heat or pulsing. Alternative chambers at an entry end of the channel are used to introduce a secondary reaction mixture or reagents. A vent to the channel provides an indication of volume of the reactants and can also function as a viewing area. Channel configurations include various paths of flow and various inner wall geometries.

36 Claims, 5 Drawing Sheets

REACTION APPARATUS EMPLOYING GRAVITATIONAL FLOW

This is a continuation of co-pending application Ser. No. 07/395,751 filed on Aug. 18, 1989, now abandoned.

BACKGROUND

In the art of laboratory chemical testing, various devices for carrying out diagnostic and other tests exist. Of particular interest today are inexpensive and preferably disposable devices which are convenient to use, yet do not dispense with the accuracy of the test performed thereby.

Currently, most disposable and/or less expensive type devices consist of two or more injection molded components which are assembled together or with other additional components. Typically, the tolerances required on the components and during assembly are very tight which contributes to high manufacturing costs. Also, many devices require during operation the application of external forces, such as mechanical agitation or a magnetic field for mixing reactants, to induce the desired chemical reaction. Such a requisite adds to operating costs of the devices.

For example, C. Coleman in U.S. Pat. No. 3,799,742 discloses a miniaturized unitary analytical test container. That device receives a specimen of interest in a reception chamber through a narrow first passageway. The specimen is transferred from the reception chamber to a filter or separation chamber through a second narrow passageway. From the filter, the specimen flows into two reaction chambers through respective conduits to the reaction chambers. A predefined amount of desired reagents are prepackaged in the reaction chambers, i.e. during manufacturing. Lead bead elements are also placed in the reaction chambers during manufacturing and act to facilitate mixing of the filtered specimen and reagent material in the chambers with application of external forces for mixing (e.g. mechanical agitation or a magnetic field). Such mixing makes the desired chemical reaction possible.

In another example, U.S. Pat. No. 4,775,515 to Cottingham discloses a device for carrying out an immunochemical particle agglutination reaction without the necessity of shaking, rocking or otherwise adding external kinetic energy thereto. The device is a slide with a channel into which liquid sample and reagents are introduced at one end. The reaction mixture is attracted to the surfaces of the channel walls and is drawn forward under capillary forces to the opposite end of the channel. During capillary flow, agglutination occurs. Coextensive with the opposite end of the channel is a viewing chamber, in which the reaction products can be observed visually or by suitable instruments. Although operating costs of this device are reasonable, manufacturing costs of the device are substantial due to the slide and channel configurations required for capillary action.

In U.S. Pat. No. 3,888,629 to Bagshawe, a testing reaction device with a predetermined amount of reactant and/or reagent contained in a porous matrix pad is disclosed. The matrix pad is supported in a container in a manner that allows sample fluid to pass from one side to another side of the pad in the container under forces of gravity. The sample fluid reacts with reactants and/or reagents contained in the matrix pad while flowing therethrough and forms a liquid product which is gathered in an end of the container and a particulate product which is retained in the matrix pad. However, such a device is costly to manufacture because different matrix pads with various reagents and/or reactants are needed for desired various reactions. Further, this type of device is not appropriate for many reaction types. The device is designed mainly for use with radioimmunoassay systems.

Accordingly, there is a need for an inexpensive and preferably disposable device useful for carrying out assays, including diagnostic tests.

SUMMARY OF THE INVENTION

The present invention provides an inexpensive and disposable reaction apparatus for detecting an analyte of interest in a liquid sample. In particular, the present invention provides an apparatus which does not require costly configurations during manufacturing and operates without a mechanically generated external force.

Specifically, the reaction apparatus of the present invention includes a housing having a channel therethrough. One end of the channel is adapted to receive reactants (i.e., a liquid sample and one or more reagents) of a test or assay to be carried out. A portion of the channel spaced from the one end (or herein referred to as the opposite end of the channel) is adapted to receive and assess the substances which are the result of the assay carried out in the apparatus. Initially, the channel is positioned horizontally, that is orthogonal with respect to the non-horizontal axes along which forces of gravity act. While the channel is in this position, the liquid sample and reagent(s) are introduced into the one end of the channel at an entry port. This combination is referred to as a reaction mixture. Thereafter due to the geometrical configuration of the channel, forces of gravity cause the reaction mixture to flow within the channel.

Specifically in a preferred embodiment the channel is inclined with respect to the axis which is orthogonal to axes along which forces of gravity act to cause the reaction mixture to flow from the one end of the channel to the opposite end of the channel, under the forces of gravity. The mixture flows in a manner which generates the necessary energy to cause physical and chemical changes in the reactants to occur in the channel. In another embodiment, the geometric configuration of the channel includes an entry portion which holds the reaction mixture with a head height above the height of the remaining portions of the channel in its initial position. In turn, gravity generates a head pressure on the reaction mixture in the entry portion of the channel and causes the reaction mixture to flow through the channel. Thus, the head height contributes to flow in the channel. The greater the head height, the greater is the contribution to flow. This contribution to the flow is minor with respect to that caused by an incline of the channel.

The channel is long enough such that the reaction occurs by the time the reaction mixture reaches the opposite end of the channel. After passing through the channel, some or all of the reaction mixture passes into the viewing chamber at the opposite end of the channel, where the results are assessed visually or by other means.

A vent in the housing provides fluid communication between the channel and the environment surrounding the housing. The vent enables flow of the reaction mixture in the channel by displacing air from within the channel to the surrounding environment. In a preferred embodiment, the vent is configured to provide an indication of volume of reactants in the channel. Further, the vent enables regulation of the velocity of the flow of the reaction mixture in the channel.

In a preferred embodiment, the one end of the channel is adapted, for example, by an entry chamber and port, to receive reactants (i.e., the sample and reagent(s)) of a desired chemical reaction. Connected to the opposite end is a chamber for receiving and holding the results of the chemical reaction as well as for assessing the results of (presence/absence and/or extent of) the reaction of components of the reaction mixture. Further, at least the channel, that is the portion of the housing forming the channel, is transparent to allow the reaction mixture to be viewed throughout flow within the channel and to allow detection of the results of the chemical reaction at the opposite end of the channel, at the viewing window.

The housing is a thin plate-like or slide member having a frontal surface and a back surface. The back surface is opposite the frontal surface across a thickness of the plate member. At least one channel is formed within that thickness between the frontal and back surfaces.

The rate of flow of the reaction mixture in the channel is dependent on several factors including humidity, temperature, coefficient of friction between the reaction mixture and the walls of the channel, and the volume of the reaction mixture. In particular, the rate of flow changes with variation in the angle of inclination of the channel in the device. The device may be inclined to form an angle between about 1° and 90° with the axis orthogonal to the axes along which forces of gravity act. A smaller angle of inclination provides a longer reaction time than that provided by a larger angle of inclination.

Another factor on which rate of flow through the channel depends is the configuration of the channel. The depth of the channel affects the velocity such that the deeper the channel, the faster the flow. In a preferred embodiment, direction and velocity of flow of the reaction mixture are changed several times during passage through the channel by one or more curves or turns in the path followed by the channel. The amount of energy introduced into the reaction mixture is a function of velocity of flow of the reactants. Hence, a greater velocity of flow causes a greater amount of energy to be imparted to the reaction mixture.

Various configurations of the inner walls of the channel are also employed to vary turbulence and, hence, impart more mixing to the reaction mixture than is generated by passage through a smooth walled channel. Such configurations include, but are not limited to, protrusions into the flow path of the reactants, ribbed walls of the channel and roughed wall surfaces.

In another embodiment of the present invention, one or more chambers connectable to the end of the channel through respective frangible seals are provided. Each chamber holds a predetermined amount of a desired reagent. Upon breakage of the frangible seal the reagent combines with the reaction mixture passing through the channel. The resulting reaction mixture (i.e., the initial reaction mixture plus additional reagent(s)) flows through the channel, the desired reaction occurs and some or all of the reaction mixture passes to the opposite end of the channel and into the area, referred to as the viewing chamber, adapted to receive the products of the reaction.

In another embodiment of the present invention, a second entry port into the channel is provided. The second or supplemental entry port receives additional reagent(s), which enters the channel, passes along the length of the channel and into the viewing chamber, in which combination with the initial reaction product occurs.

In another embodiment of the present invention, a second channel is provided in the housing. The second channel has a first end for receiving selected reagents for a control reaction and has an opposite end adapted to receive the products of the control reaction. The control reaction is performed in the second channel to provide a standard against which the reaction in the first channel is compared. The second channel also has a vent for enabling and regulating flow of the selected control reagents therein.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The reaction apparatus of the present invention is adaptable for use in a broad range of tests, including tests for blood glucose, urea, uric acid, blood alcohol, enzymes, ketones, silicates, hemoglobin, cholesterol, fibrinogen, immunological tests and a wide range of additional tests. Also, the apparatus of the present invention is adaptable to be employed with a wide range of human and animal specimens including, but not limited to, blood, urine, milk, saliva, sweat, spinal fluid, amniotic fluid and other biological and non-biological materials. In the interest of simplicity and clarity of the following description, each of the discussed structural embodiments is understood not to be limited to specific tests and/or specimens and may employ a wide range thereof.

Figure 1:
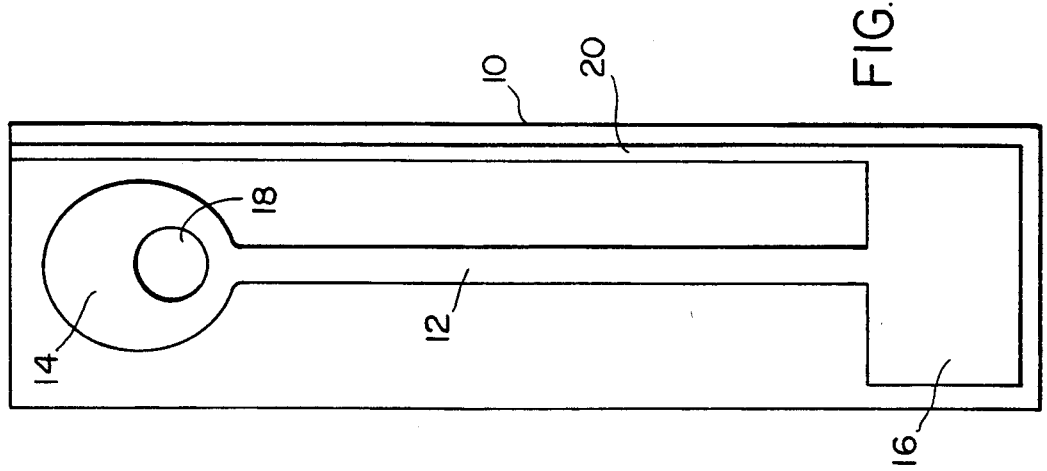
FIG. 1 is a schematic view of one of the simplest embodiments of the present invention.

Perhaps the most basic terms of the present invention are illustrated in the embodiment of FIG. 1. That embodiment provides a plate-like member or slide 10 which serves as a housing. Within the plate-like member 10 is a channel 12. An entry chamber 14 with an entry port 18 through the plate-like member is coupled to one end of the channel 12, and the opposite end of the channel opens into a viewing chamber 16, described later.

With the slide positioned such that the channel 12 is generally horizontally level, reactants (i.e., a sample to be analyzed for analyte(s) of interest and selected reagent(s) (those appropriate for the test to be carried out)) are introduced into the entry chamber 14 through entry port 18 by means of a pipet, dropper or inoculating loop, for example. The reactants are introduced along an axis that is generally perpendicular to the plate-like member 10 such that the reactants make contact with the portion of the plate like member opposite the entry port 18 across the entry chamber 14 at an angle of about 90°.

The reactants are initially mixed together in the entry chamber 14. The reactants alternatively may be mixed with reagents of various formats or diluted as desired before being introduced into the entry chamber 14.

After the introduction into and/or mixing of the reactants in the entry chamber 14, the plate-like member 10 is placed on an incline of between about 1° and 90° with respect to an axis orthogonal to axes along which forces of gravity act. At this inclined position, gravity acts on the reactants in the entry chamber 14 and initiates flow of the reactants into the channel 12. As the reactants flow in the channel 12 along the length of the channel 12, the fluid mixture picks up momentum. With this momentum, kinetic energy is generated in the flowing fluid in an amount sufficient to bring about a chemical and/or physical reaction between the flowing reactants. Results of the reaction (i.e., reaction products and/or unreacted reactants) are retained in the viewing chamber 16 at the end of the channel 12 and/or are viewable through the transparent walls of the channel 12 during flow of the reactants.

The viewing chamber 16 is transparent such that results of the chemical reaction are visibly determined through the viewing chamber. The viewing chamber 16 may have a volume which approximates the volume of the channel 12, or the viewing chamber 16 may be of a variety of sizes and shapes depending on the nature of the reaction results to be viewed. Visible reaction indications include, but are not limited to, formation or lack of formation of agglutinates, the occurrence or absence of a color change, or other physical changes. Detection methods and means common in the art may be used to inspect the reaction results in the viewing chamber 16.

In some instances, after the introduction of reactants into the entry chamber 14, the plate-like member 10 may be left such that the channel 12 is generally horizontally level (i.e. the slide is not placed on an incline). In this position, a sufficient volume of the reactants forms a head height in the entry chamber 14 that is above the height of the walls of the channel 12 with respect to the surface on which the slide lies. With such a head height, the forces of gravity create a head pressure on the reactants in entry chamber 14. The head pressure causes the reactants to flow from the entry chamber 14, through the channel 12, to viewing chamber 16. Hence, a gravity induced flow is created and potentially imparts necessary energy to bring about a reaction between the flowing reactants in channel 12. Results of any reaction are observable through the walls of channel 12 during flow as well as through viewing chamber 16 as described above.

To enable the reactants to flow through the channel 12, vent 20 allows displacement of air from the channel to the surrounding environment of the apparatus. To that end, the size of vent 20 enables regulation of the velocity of the flow of the reactants in channel 12. Further, the flow time of the reaction mixture through the channel 12 is determined by, among other factors, channel configuration, head height of the reactants in the entry chamber 14, incline angle, the vent size, the reactants used, coefficient of friction between the channel walls and the reactants, the material of manufacture of the apparatus, temperature of the reactants and humidity.

The design configuration of the present invention enables a sufficient amount of kinetic energy to be imparted to the reaction mixture such that the desired reaction is completed when the fluid (reaction mixture) enters the viewing chamber 16. Kinetic energy is imparted to the reaction mixture by several fluid phenomena. The fluid phenomena include, but are not limited to, drag forces, shearing stress, fluid acceleration, and velocity contours. With respect to velocity, the greater the velocity of the fluid is, the greater is the amount of kinetic energy generated. To that end, reaction time is varied as a function of incline angle of channel 12 where a change in incline angle alters the effect of gravity on velocity of the flowing reaction mixture.

Alternatively, the angle of incline may be changed during the running of the reaction to vary flow time. For example, the plate member may be held in a rocker or other rocking means which varies angle of incline between a range of angles.

The channel 12 has internal dimensions of a depth of about 0.003 to 0.050 inch and a width of about 0.010 to about 0.200 inch. The minimal length of the channel 12 differs for different desired reactions but is generally about 1.5 to 9 inches. The channel path may be configured to run longitudinally, as in FIG. 1, or to traverse across the plate member 10 to vary the velocity of the fluid, as illustrated in FIGS. 2 and 3, or to run at an angle as in FIG. 3.

Figure 2:
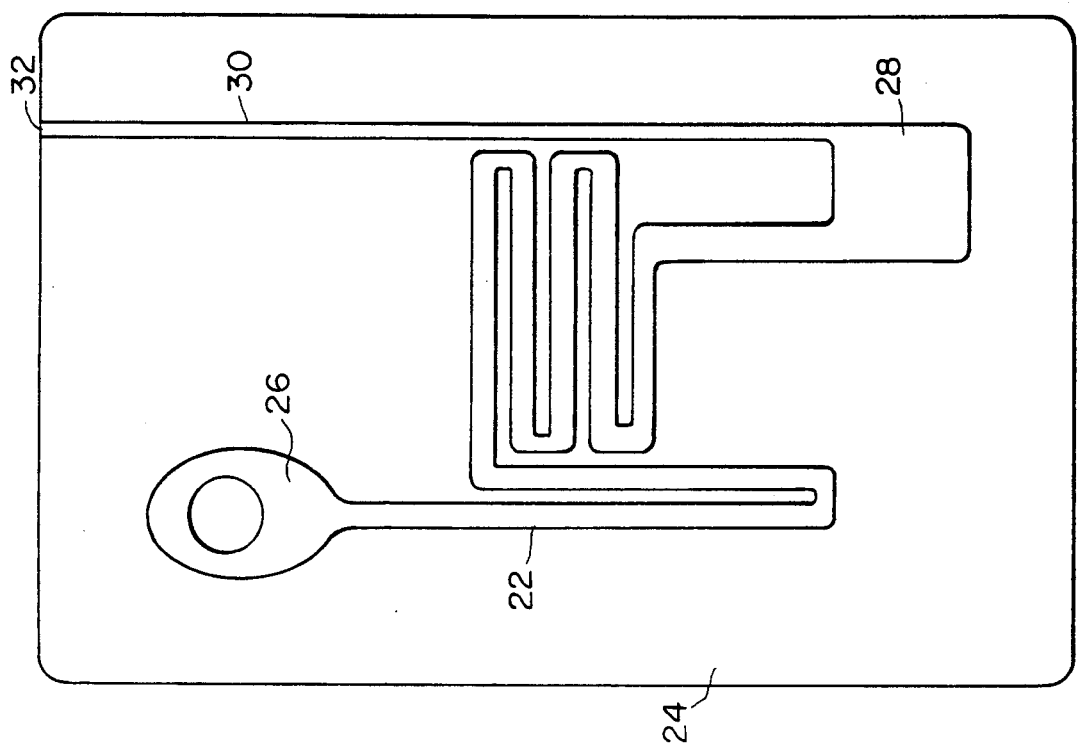
FIG. 2 is a schematic view of another embodiment of the present invention.
Figure 3:
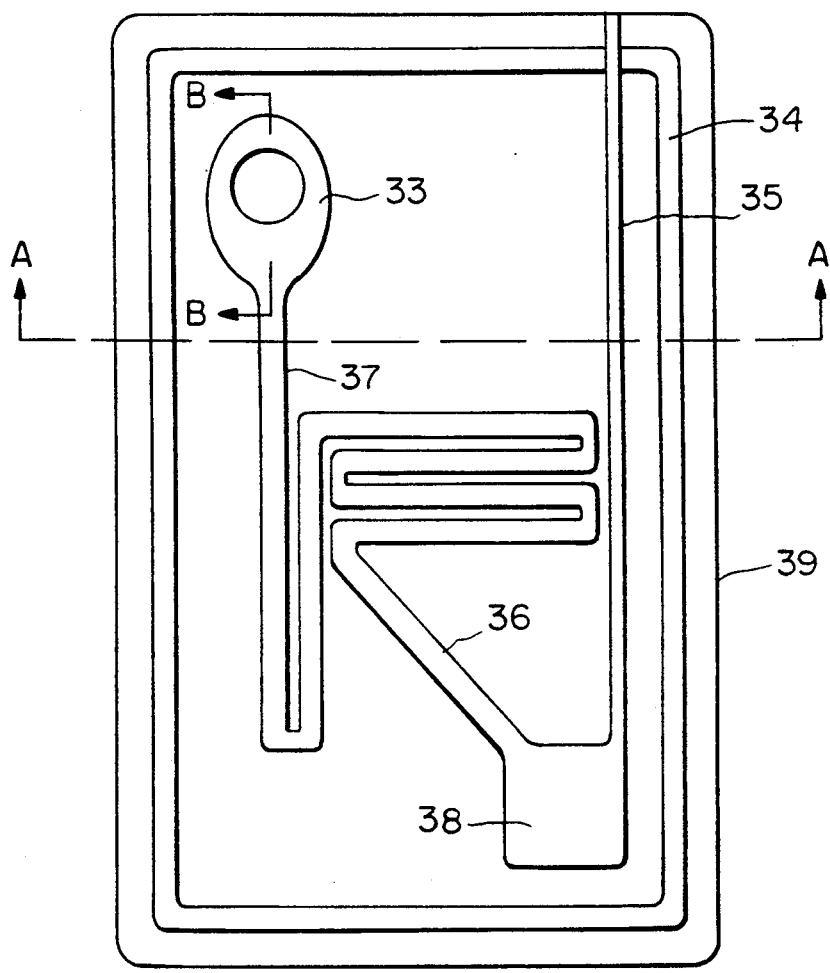
FIG. 3 is a schematic view of an embodiment of the present invention with an angled channel portion for magnetic testing.

The channel illustrated in FIG. 2 has various segments which run longitudinally along portions of the plate member 24 as well as horizontally along the portions of the plate member. The channel segments are serially connected end to end with elbow or curved sections to provide a continuous channel 22 from the entry chamber 26 to the viewing chamber 28.

Also, the vent 30 is itself a channel from the viewing chamber 28 to an opening 32 in the plate member 24. The vent 30 is configured in this manner such that when the viewing chamber 28 is filled with reaction fluid, the fluid rises into the vent channel and the height of the fluid in the vent channel is indicative of fluid volume. This indication of fluid volume verifies that a correct volume of reaction mixture was used. Further, the vent 30 can be used as a viewing chamber.

Use of and the gravity flow induction of a reaction in the apparatus of FIG. 2 is then as described above in the embodiment of FIG. 1. The embodiment of FIG. 2 is configured for latex agglutination reactions, for example.

FIG. 3 provides an embodiment of the present invention which operates in a manner similar to that of the foregoing embodiments, but provides an angled channel segment 36 which delivers reaction products into the viewing chamber 38. The angled channel segment 36 provides an isolated area in which to place a magnet for magnetic capture of reaction products. Procedures for magnetic capture are known in the art and generally described in U.S. patent application Ser. No. 07/189,983 for a "Capillary Flow Device and Double Capture Assay Method for Use in Same" and assigned to the assignee of the present invention, now abandoned. Hence, the FIG. 3 embodiment of the present invention is suited for carrying out antigen-antibody specific binding assays, for example, of drugs, hormones and etc.

Figure 3A:
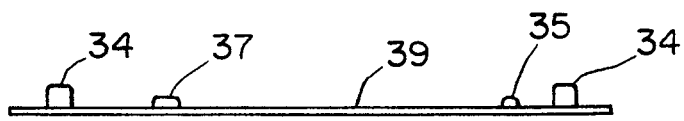
FIG. 3a is a cross-section along line A—A in FIG. 3.

Further, the apparatus in FIG. 3 has a supporting rib 34 around its outer periphery for structural support. As shown in cross-section in FIG. 3a, rib 34 protrudes from the plate member 39 a greater distance (i.e. has a greater depth) than do channel 37 and vent 35. This rib 34 may be included in other embodiments as desired.

Figure 3B:
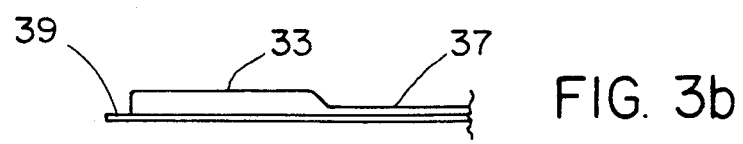
FIG. 3b is a partial section along line B—B in FIG. 3.

Also FIG. 3b illustrates the protrusion/depth configuration of the entry chamber 33 relative to that of the channel 37 with respect to plate member 39.

Figure 4:
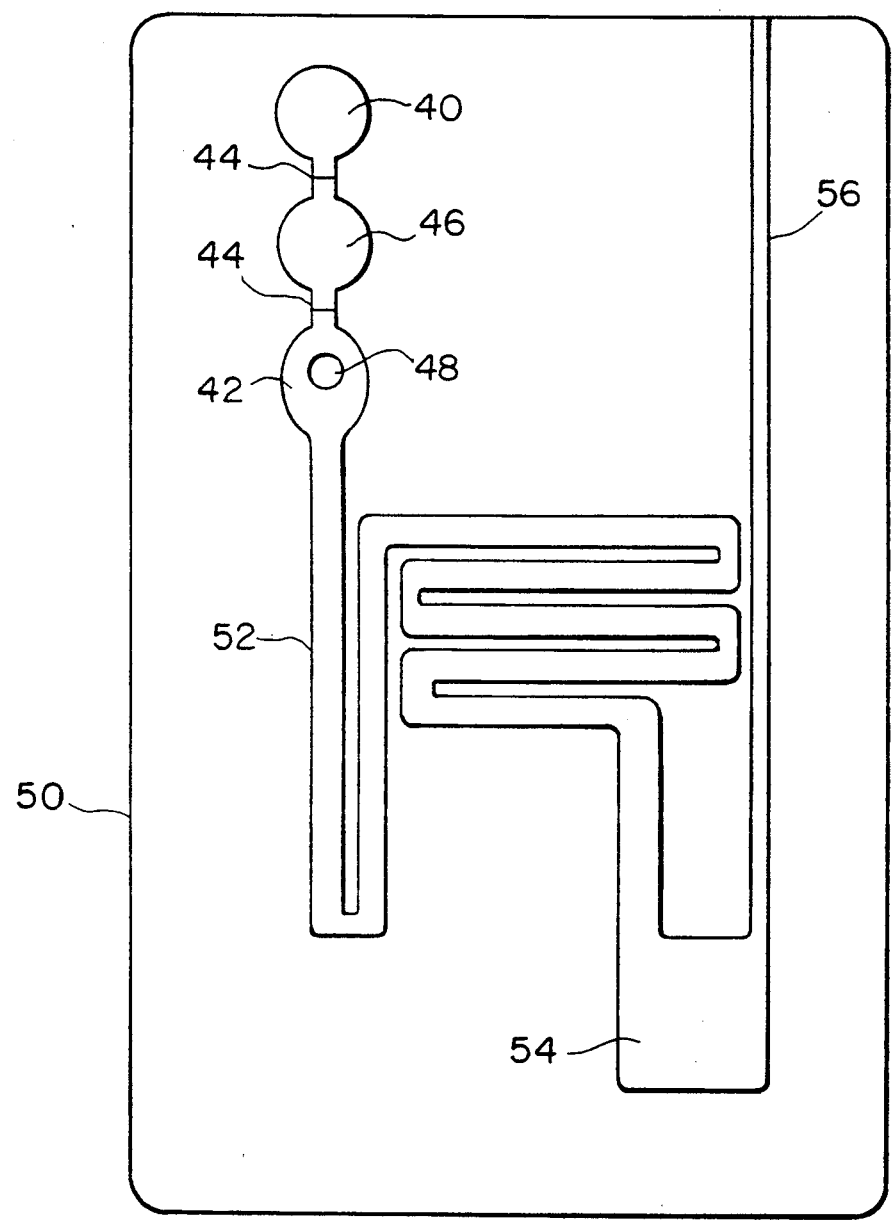
FIG. 4 is a schematic view of another embodiment of the present invention with reagent-containing chambers separated by frangible seals.

FIG. 4 provides an embodiment which employs two working chambers 40, 46 serially connected or otherwise connected to the entry chamber 42. Each working chamber 40, 46 is separated from an adjacent working chamber and/or the entry chamber 42 by a frangible heat seal 44. Desired reagents, such as a liquid reagent in working chamber 40 and a powdered reagent in working chamber 46, are pre-measured and positioned in the working chambers during manufacturing. During use, the desired reactants are introduced into entry chamber 42, and the frangible heat seals 44 are broken, for example by applying pressure on working chambers 40 and 46, with the plate member 50 in its horizontally level position (i.e., before being placed in an inclined position). Upon inclination of the plate member 50, reagents flow into the entry chamber 42 to mix with the sample introduced through the entry port 48 in the entry chamber 42. The reagents and sample flow together through the channel 52 under the forces of gravity and mix with each other. Also during flowing, the reaction mixture gains momentum, which in turn imparts the necessary kinetic energy to bring about the desired reaction of the flowing fluids. Results (i.e., products) of the reaction are retained in viewing chamber 54 while vent 56 allows fluid flow through the channel 52 by displacing air therein.

Such a configuration of the present invention as illustrated in FIG. 4 is useful for unit dose packaging of latex agglutination assays, e.g. for drugs of abuse assays.

Figure 5A:
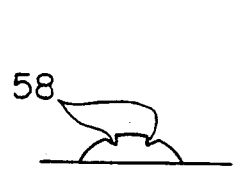
FIGS. 5a–5c are cross section and plan views of channel configurations for the present invention.
Figure 5B:
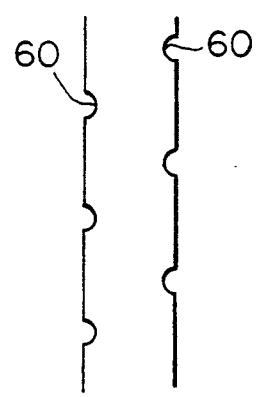
Figure 5C:
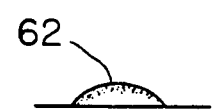

Various channel configurations will impart more mixing of the reaction mixture during flow through the channel than a channel formed by smooth walls. FIGS. 5a-5c illustrate some of the different channel configurations which are employable in the present invention. It is understood that other channel configurations are suitable.

Shown in FIG. 5a is a cross-section of a ribbed channel which is made by known means. The ribs 58 enter into the fluid pathway and alter the flow path. Alterations of the flow path causes localized eddies or currents which increase mixing of the flowing fluids.

FIG. 5b, a plan view, illustrates a channel with protrusions 60 staggered along facing inner walls of the channel. The protrusions 60 reduce the internal channel width at given locations which in turn alters local velocity of fluid flow. This alteration of velocity increases the amount of mixing imparted to the reaction mixture. Such a channel is manufactured by known methods and means.

FIG. 5c is a cross-section of a channel having rough surfaces 62 along its inner walls. The rough surfaces alter the flow path and increases mixing of the flowing fluids in a similar manner as that with the ribbed channel of FIG. 5a. The rough surfaces are manufactured by known methods and means.

Figure 6:
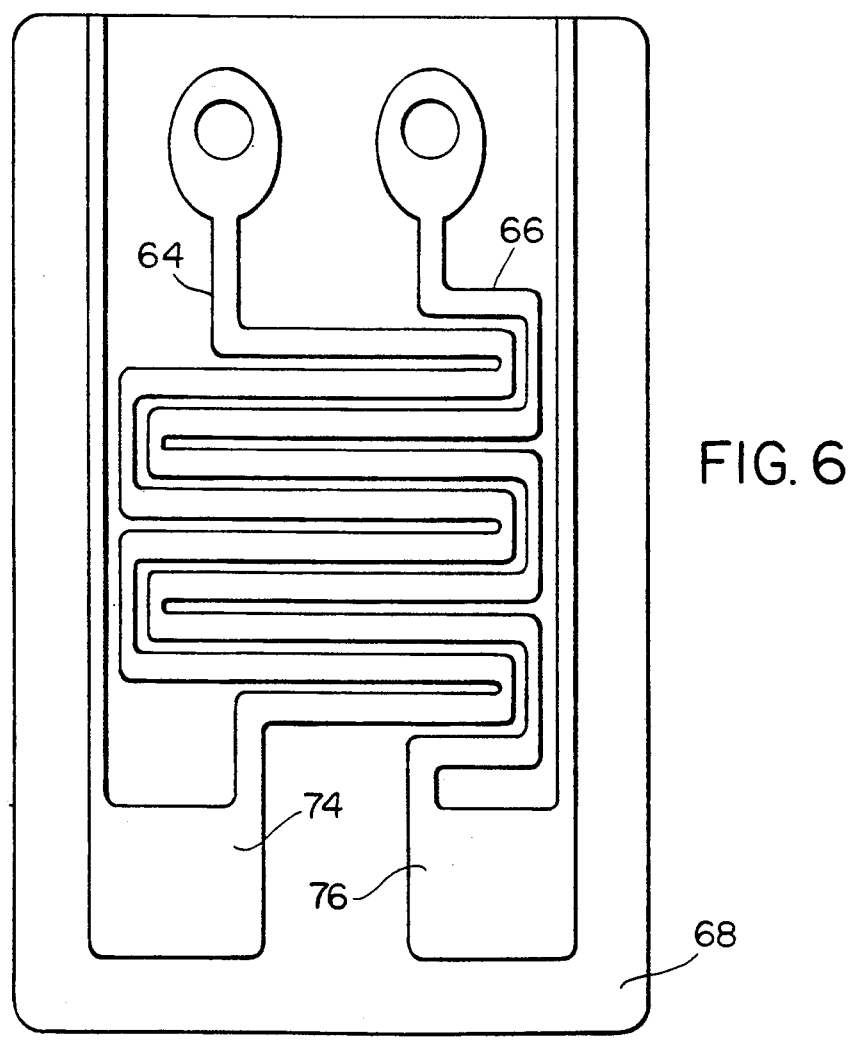
FIG. 6 is a schematic view of an embodiment of the present invention which enables a control reaction to be performed alongside a test reaction.

Provided in FIG. 6 is an illustration of an embodiment with two independent channels 64, 66 for performing separate flow reactions. A control assay is run in one channel (for example, channel 66) and an assay for an analyte of interest in a sample is run in the second channel (for example, channel 64). The appropriate reactants for the control reaction are introduced into one channel (e.g., channel 66), and the sample to be analyzed and appropriate reagents are introduced into the other channel (e.g., channel 64). The plate member or slide 68 which houses the channels 64, 66 is thereafter oriented with respect to an axis orthogonal to axes along which forces of gravity act such that the fluids of the control assay flow through the one channel (channel 66), and the desired reactants of the subject chemical reaction flow through the other channel (channel 64). Products of the reactions are retained in the respective viewing chambers 74, 76 of the channels 64, 66 and are able to be compared visually or by other means through the viewing chambers.

The embodiment of FIG. 6 is useful for visually inspected immunoassays, where it is useful to compare the unknown result to the outcome of a known reaction. Rapid immunoassays for drugs of abuse are an example.

Figure 7:
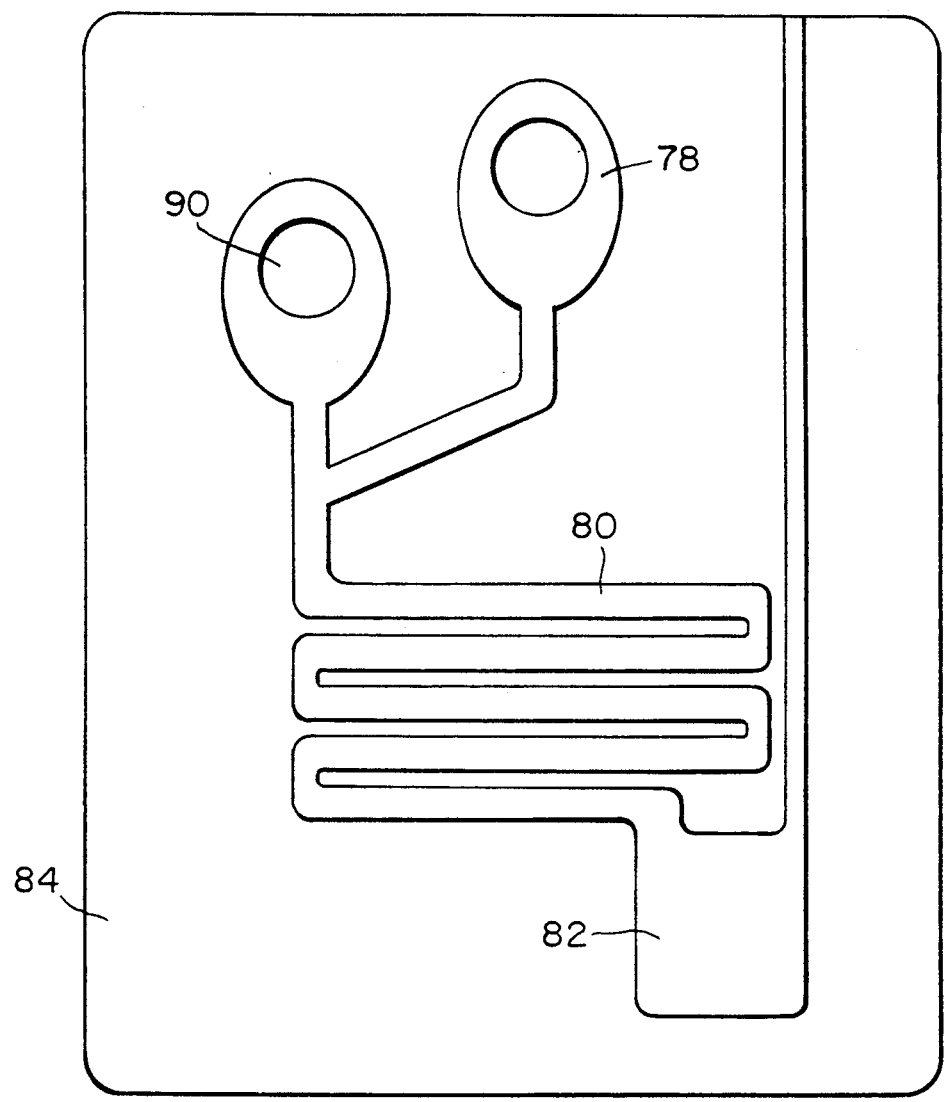
FIG. 7 is a schematic view of an embodiment of the present invention with a supplemental entry port.

FIG. 7 provides an illustration of an embodiment by which additional reagent(s) can be added to the results of a first reaction mixture by means of a supplemental entry port and chamber assembly 78. After the sample and reagent(s) of a first reaction mixture introduced into the apparatus at entry port 90 have flowed through the channel 80 to the viewing chamber 82, the additional reagent(s) is/are introduced into the entry port of the supplemental entry assembly 78 while the plate member 84 is in its inclined position. Gravity pulls the secondary reaction mixture through the channel 80 in a manner which imparts kinetic energy into the additional reagent(s). As a result, the additional reagent(s) pass into viewing chamber 82, where the desired reaction mixes with the results of the initial reaction.

This embodiment is useful for any assay where stepwise addition of components is required—e.g. an EIA assay where substrate addition occurs late in the reaction, or an assay where a "stop solution" is added to stabilize the assay result.

Embodiments of the present invention are economically fabricated using various existing processing including, but not limited to, injection molding, thermoforming, blow molding, cold forming, heat sealing and ultrasonic welding. The materials used in the embodiments include, but are not limited to, polystyrene, polycarbonate, polypropylene, polyvinylchloride, polyethylene, acrylic, polyester, coated paper and coated foils.

Manufacture of the embodiments of the present invention is generally as follows: A 0.010 inch thick sheet or layer of clear rigid PVC or other plastic is cut to desired outer dimensions, for example about 3 to 4 inches by about 0.7 to 2.5 inches with rounded corners of about 0.010 radius of curvature. This forms a first slide or plate piece.

The desired configurations for the entry chamber and port (main and secondary), channel(s), viewing chamber, vent and reagent chambers are then formed in the first plastic piece by one of the above-mentioned techniques. For example, a narrow groove about 0.010 to about 0.20 inch wide by about 0.003 to about 0.050 inch deep is thermoformed into the plastic plate piece. The groove is made to follow a path which is patterned as desired (e.g. a longitudinal straight path, a path which traverses, turns, or curves across the width of the plastic piece one or more times, or a combination thereof). Also, the groove can be made with protrusions, ribs or rough walls such as those illustrated in FIGS. 5a-5c, as desired. At the end of the groove that will serve as an entrance into which reactants are introduced, a well-like or pit area is formed. For example, an oblong grooved area of about 0.50 inch by about 0.75 inch is formed. At the opposite end of the narrow groove, the viewing chamber is formed by a well or pit type groove.

Also, a support rib as desired is formed into the first plastic piece about the periphery of the piece. The groove is about 0.010 to about 0.20 inch wide and about 0.006 to about 0.10 inch deep.

A hole of about 0.30 inch in diameter is drilled or punched into the entry chamber from the first plastic piece side to provide an entry opening or port. Alternatively, the entry chamber remains sealed on all sides for anti-contamination purposes. A perforated circular line is instead formed in the first plastic piece side of the entry chamber. At the time of use, the area within the perforated line is removed to gain entry into the entry chamber.

A second clear plastic piece is cut from a second layer of plastic. The second plastic piece is cut to match the outer or peripheral dimensions of the first plastic piece. The second plastic piece is heat sealed or otherwise attached to the groove side of the first plastic piece to form between the two pieces an enclosed channel for fluid flow, entry chamber(s), viewing chamber(s), vents, reagent chambers and a supporting rib, if desired.

The reagent chambers are filled with measured amounts of desired reagents before the second plastic piece is sealed to the first plastic piece. The frangible seals between reagent chambers are then formed, for example, by creating a weak heat seal between the portions of the two plastic pieces which make contact at the positions between the reagent chambers.

Figure 8:
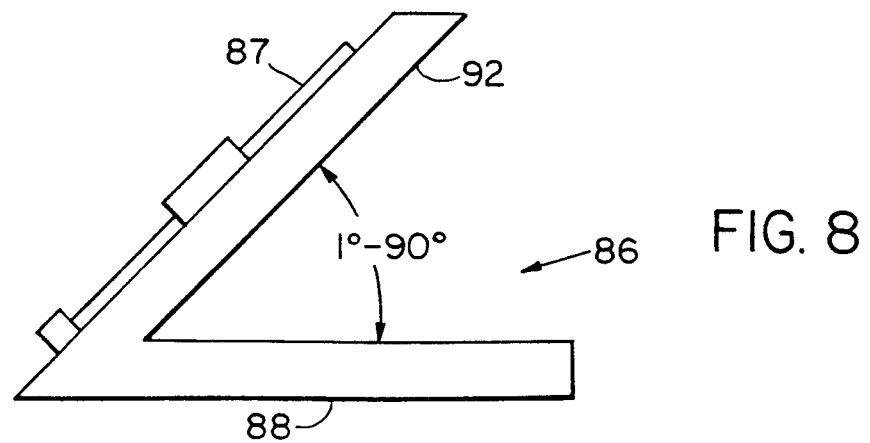
FIG. 8 is a schematic illustration of operation of an embodiment of the present invention on a support block which provides angles of inclination between 1° and 90° with respect to an axis orthogonal to axes along which forces of gravity act.

FIG. 8 provides an illustration of a support block or stand 86 which is to be used with the embodiments of the present invention. The support block 86 has a base portion 88 and a working portion 92. The base portion 88 sits on a desired work surface such as a table top. The working portion 92 is positioned with respect to base portion 88 to form an angle therebetween about 1° to about 90°. This internal angle provides an angle of incline with respect to the axis orthogonal to the axes along which forces of gravity act. A slide device 87 of the present invention is removeably attached with a back surface of its plate member against the outer surface of the working portion 92 of the support block 86. The slide device 87 and, hence, the channel therein thereby assumes the angle of incline of the support block 86 such that a reaction mixture flows in the channel at this angle.

Support block 86 may be manufactured from wood, plastic, or other materials in which the desired angle of incline and width of the outer surface of working portion 92 are formed. Slots, a ledge for supporting slide device 87, and/or other members for holding device 87 to working portion 92 are attached to support block 86 by common methods. Such members are manufactured from suitable materials and means.

Preferably, an angle of incline is predetermined for each particular slide device of the present invention such that the flow time of a certain reaction mixture through the channel of the device positioned at the predetermined angle is the reaction time for the reaction mixture. Thus, different support blocks with different angles of incline may be used with respective slide devices of the present invention which carry out particular reactions at certain angles of operation in a certain amount of time. To that end, the channel of each such slide device is configured such that flow time of the particular reaction mixture is the amount of time required for reaction to occur. As a result, a slide device of the present invention with a respective support block for a particular angle of incline provides means and a method for carrying out a reaction between certain reactants without the necessity of a timer (i.e. watch or clock).

Equivalents

While the invention has been particularly shown and described with reference to a preferred embodiment thereof, it will be understood by those skilled in the art that various changes in form and details may be made therein without departing from the spirit and scope of the invention as defined by the appended claims.

I claim:

1. A reaction apparatus comprising:
   a housing including an inclinable plate member;
   at least a first non-capillary channel in the plate member, said first channel having an entry end and a viewing end spaced apart from each other, the entry end having means for receiving reactants of a selected reaction, and the first channel having a geometric configuration which includes a path between the entry and viewing end and a substantially uniform width along the path;
   a first vent in the housing connected to the first channel, the first vent providing fluid communication between the first channel and the environment surrounding the housing to enable fluid flow of the reactants in the first channel; and
   a separate support means to support the plate member such that the first channel has an angle of incline with respect to a horizontal plane, wherein the angle of incline, in conjunction the path of the first channel create a flow of the reactants in the first channel.

2. The apparatus as claimed in claim 1, wherein the path of the first channel includes curved and straight sections.

3. The apparatus as claimed in claim 1, wherein the angle of incline with respect to the horizontal plane is between about 1° and 90°.

4. The apparatus as claimed in claim 1, wherein the separate support means is a support block which holds the plate member at the angle of incline.

5. The apparatus as claimed in claim 1, further comprising:
   an entry chamber coupled to the entry end of the first channel; and an entry port in the housing in communication with the entry chamber, the entry port enabling the reactants to be introduced into the first channel through the entry chamber.

6. The apparatus as claimed in claim 5, wherein the entry chamber and the first channel are positioned along a common plane through the housing, the entry chamber shaped to provide a height dimension, above the plane of the first channel.

7. The apparatus as claimed in claim 1, further comprising a viewing chamber in the housing coupled to the viewing end of the first channel for receiving and holding the results of the reaction to provide a view thereof.

8. The apparatus as claimed in claim 1, wherein the plate member comprises a frontal surface and a back surface wherein at least one of the frontal and back surfaces is substantially transparent such that the reactants are viewable within the first channel through the length of the first channel.

9. The apparatus as claimed in claim 1, wherein the first vent has a configuration that provides an indication of the volume of reactants used in the first channel.

10. The apparatus as claimed in claim 1, wherein the first vent is sized to provide regulation of the flow of the reactants in the first channel.

11. The apparatus as claimed in claim 1, wherein the plate member has longitudinal and transverse dimensions and the first channel consists of a plurality of segments including a first segment which runs longitudinally from the entry end, additional segments, a portion of which run transversely as well as longitudinally and a final segment which runs substantially longitudinally into the viewing end, said segments serially connected end to end by elbow sections to provide a continuous, uninterrupted channel, such that there are changes in direction and velocity of the flow of the reactants in the first channel.

12. The apparatus as claimed in claim 1, wherein the first channel comprises materials which enable different flow velocities of the reactants in the first channel.

13. The apparatus as claimed in claim 1, wherein the first channel has inner walls with a plurality of protrusions that provide mixing of the reactants in the first channel.

14. The apparatus as claimed in claim 1, further comprising at least one reagent chamber in the housing connected to the entry end of the first channel by a respective frangible seal, each reagent chamber holding a reagent to be mixed with the reactants upon breakage of the respective frangible seal.

15. The apparatus as claimed in claim 1, further comprising a secondary entry chamber connected to the first channel for receiving a secondary reaction mixture which flows through the first channel to the viewing end.

16. The apparatus as claimed in claim 15, wherein the first vent is sized to provide regulation of the flow of the reactants in the first channel.

17. The apparatus as claimed in claim 1, further comprising:
a second non-capillary channel in the plate member, said second channel having an entry end and a viewing end spaced apart from each other, the entry end having means for receiving predefined reactants of a control reaction; and
a second vent in the housing connected to the second channel to enable fluid flow of the control reactants therein.

18. The apparatus as claimed in claim 17, wherein the first and second vents are sized to provide regulation of the flow of the reactants in the first and second channels.

19. A chemical reaction apparatus comprising:
an inclinable plate member having a frontal surface and a back surface opposite the frontal surface across a thickness of the plate member, the plate member having an inoperative position on a horizontal plate and an operative position at an angle of incline with respect to the horizontal plate;
at least a first non-capillary channel formed between the frontal end and back surfaces of the plate member, said first channel having an entry end and a viewing end spaced apart from each other, the entry end having means for receiving desired reactants of a reaction, and the first channel having a geometric configuration which includes a path between the entry and viewing ends and a substantially uniform width along the path;
a first vent in the housing connected to the first channel, the first vent providing fluid communication between the first channel and the environment surrounding the housing to enable fluid flow of the reactants in the first channel; and
a separate support means to support the plate member at the operative position, wherein the angle of incline, in conjunction the path of the first channel create a flow of reactants in the first channel.

20. The apparatus as claimed in claim 19, wherein the path of the first channel includes curved and straight sections.

21. The apparatus as claimed in claim 19, wherein the angle of incline with respect to the horizontal is between about 1° and 90°.

22. The apparatus as claimed in claim 19, further comprising an entry chamber connected to the entry end of the first channel, the entry chamber enabling the reactants to be introduced into the first channel.

23. The apparatus as claimed in claim 22, wherein the entry chamber and the first channel are positioned along a common plane through the housing, the entry chamber shaped to provide a height dimension, above the plane of the first channel.

24. The apparatus as claimed in claim 19, further comprising a viewing chamber in the plate member connected to the viewing end of the first channel for receiving and holding the results of the chemical reaction in a manner that provides a view the chemical reaction.

25. The apparatus as claimed in claim 19, wherein at least one of the frontal and back surfaces is substantially transparent such that the reactants are viewable within the first channel throughout the length of the first channel.

26. The apparatus as claimed in claim 19, wherein the first vent has a configuration that provides an indication of the volume of reactants used in the first channel.

27. The apparatus as claimed in claim 19, wherein the first vent is sized to provide regulation of the flow of the reactants in the first channel.

28. The apparatus as claimed in claim 19, wherein the first channel in the plate member follows a path that transverses across a width and length of one of the frontal and back surfaces of the plate member.

29. The apparatus as claimed in claim 19, wherein the plate member has longitudinal and transverse dimensions and the first channel consists of a plurality of segments including a first segment which runs longitudinally from the entry end, additional segments, a portion of which run transversely as well as longitudinally and a final segment which runs substantially longitudinally into the viewing end, said segments serially connected end to end by elbow sections to provide a continuous, uninterrupted channel, such that there are changes in direction and velocity of the flow of the reactants in the first channel.

30. The apparatus as claimed in claim 19, wherein the first channel comprises materials which enable different flow velocities of the reactants in the first channel.

31. The apparatus as claimed in claim 19, wherein the first channel has inner walls with a plurality of protrusions that provide mixing of the reactants in the first channel.

32. The apparatus as claimed in claim 19, further comprising at least one reagent chamber in the housing connected to the entry end of the first channel by a respective frangible seal, each reagent chamber holding a reagent to be mixed with the reactants upon breakage of the respective frangible seal.

33. The apparatus as claimed in claim 19, further comprising a secondary entry chamber connected to the first channel for receiving a secondary reaction mixture which flows through the first channel to the viewing end.

34. The apparatus as claimed in claim 33, wherein the first vent is sized to provide regulation of the flow of the reactants in the first channel.

35. The apparatus as claimed in claim 19, further comprising:
- a second non-capillary channel in the plate member, said second channel having an entry end and a viewing end spaced apart from each other, the entry end having means for receiving predefined reactants of a control reaction; and
- a second vent in the housing connected to the second channel to enable fluid flow of the control reactants therein.

36. The apparatus as claimed in claim 35, wherein the first and second vents are sized to provide regulation of the flow of the reactants in the first and second channels.

* * * * *

UNITED STATES PATENT AND TRADEMARK OFFICE
CERTIFICATE OF CORRECTION

PATENT NO. :  5,225,163
DATED       :  July 6, 1993
INVENTOR(S) :  Robert R. Andrews It is certified that error appears in the above-identified patent and that said Letters Patent is hereby corrected as shown below:

Column 10, Claim 1, line 9 of that claim after "viewing" change "end" to read ---ends---.

Column 12, Claim 19, lines 5 and 6 of that claim after "horizontal" change "plate" to read ---plane---.

Column 12, Claim 24, line 5 of that claim after "view" and before "the" insert ---of---.

Signed and Sealed this

Twenty-fourth Day of May, 1994

Attest:

BRUCE LEHMAN

*Attesting Officer*   Commissioner of Patents and Trademarks